(12) United States Patent
Brown

(10) Patent No.: US 6,734,178 B2
(45) Date of Patent: May 11, 2004

(54) CEPHALOTAXINE ALKALOID COMPOSITIONS AND USES THEREOF

(75) Inventor: Dennis M. Brown, Menlo Park, CA (US)

(73) Assignee: ChemGenex Therapeutics, Inc., Menlo Park, CA (US)

( * ) Notice: Subject to any disclaimer, the term of this patent is extended or adjusted under 35 U.S.C. 154(b) by 0 days.

(21) Appl. No.: 09/810,527

(22) Filed: Mar. 15, 2001

(65) Prior Publication Data

US 2002/0032190 A1 Mar. 14, 2002

Related U.S. Application Data

(60) Provisional application No. 60/189,699, filed on Mar. 15, 2000.

(51) Int. Cl.[7] .................... A61K 31/55; A61K 33/24
(52) U.S. Cl. ............................ 514/214.01; 424/649
(58) Field of Search .................. 514/214.01; 424/649

(56) References Cited

FOREIGN PATENT DOCUMENTS

WO  WO 2001068098 A2 * 9/2001 ............... 424/649

OTHER PUBLICATIONS

Jin et al., Shanghai Yike Daxue Xuebao (1989), 16(1), 50–4 Abstract Only.*
Abbott et al., Cancer Research Supplement, Part 2, vol. 26, No. 9, Sep., 1966, pp 1131, 1132, 1135 and 1136.*
Visani, C., et al., "Effects of homoharringtonine alone and in combination with alpha interferon and cytosine with alpha interferon and cytosine arabinoside on "in vitro" growth and induction of apoptosis in chronic myeloid leukemia and normal hematopoietic progenitors," *Leukemia* 11:624–628 (1997).
Yuzhu, Z. et al., "Hemoharringtonine, cytarabine and aclarubicin (HAA) combination chemotherapy for acute myeloid leukemia (AML)," Chinese Journal of Clinical Oncology (1998) 25/10 pp. 758–759, retrieved from STN, Database EMBASE 'Online' Acc. No. 1998384948 Abstract.
Laster Jr., W.R. et al., "Therapeutic synergism (TS) of homoharringtonine (H) plus 5–fluorouracil (FU) against leukemia P388 (P388/o) and ARA–C–resistant P388 (P388/ARA–C)," Proc. Am. Assoc. Cancer Res. (1982), vol. 23, No. 786. retrieved from STN, Database EMBASE 'Online' Acc. No. 82182588.
Zhang, S.D. et al., "Inhibitory Effects of Homoharringtonine and Hydroxycamptothecin in Combination with Other Agents on Cancer Cell Growth," *Asia Pacific Jour Pharm* 1992, 7:191–195.
Takano, I. et al., "New Oxygenated Cephalotaxus Alkaloids from *Cephalotaxus harringtonia* var. *drupacea*," *J. Nat. Proc.* 1996, 59:1191–1195.
Takano, I. et al., "Ester–Type Cephalotaxus Alkaloids from *Cephalotxus Harringtonia* var. *Drupacea*," *Phytochemistry* 44(4):735–738 (1997).

* cited by examiner

*Primary Examiner*—Rebecca Cook
(74) *Attorney, Agent, or Firm*—Dorsey & Whitney LLP; Richard F. Trecartin; Traci H. Ropp

(57) ABSTRACT

A method of treatment of a host with a cellular proliferative disease, comprising contacting the host with a cephalotaxine and an antiproliferative agent, each in an amount sufficient to modulate said cellular proliferative disease, is described. In some embodiments, the cephalotaxine comprises homoharringtonine (cephalotaxine, 4-methyl-2-hydroxy-2-(4-hydroxy-4-methyl pentyl) butanediocate ester). Antiproliferative agents of the invention comprise alkylating agents, intercalating agents, metal coordination complexes, pyrimidine nucleosides, purine nucleosides, inhibitors of nucleic acid associated enzymes and proteins, and agents affecting structural proteins and cytoplasmic enzymes.

10 Claims, 3 Drawing Sheets

CEPHALOTAXINE ALKALOID COMPOSITIONS AND USES THEREOF

This application claims the benefit of U.S. Provisional Application No. 60/189,699, filed Mar. 15, 2000.

FIELD OF THE INVENTION

The technical field of the invention is the use of cephalotaxine alkaloids with antiproliferative agents to treat a host with a cellular proliferative disease.

BACKGROUND OF THE INVENTION

There is considerable interest in modulating the efficacy of currently used antiproliferative agents to increase the rates and duration of antitumor effects associated with conventional antineoplastic agents.

Conventional antiproliferative agents used in the treatment of cancer are broadly grouped as chemical compounds which (1) affect the integrity of nucleic acid polymers by binding, alkylating, inducing strand breaks, intercalating between base pairs or affecting enzymes which maintain the integrity and function of DNA and RNA; (2) chemical agents that bind to proteins to inhibit enzymatic action (e.g., antimetabolites) or the function of structural proteins necessary for cellular integrity (e.g., antitubulin agents). Other chemical compounds that have been identified to be useful in the treatment of some cancers include drugs which block steroid hormone action for the treatment of breast and prostate cancer, photochemically activated agents, radiation sensitizers and protectors.

Of special interest to this invention are those compounds that directly affect the integrity of the genetic structure of the cancer cells. Nucleic acid polymers such as DNA and RNA are prime targets for anticancer drugs. Alkylating agents such as nitrogen mustards, nitrosoureas, aziridine containing compounds directly attack DNA. Metal coordination compounds such as cisplatin and carboplatin similarly directly attack the nucleic acid structure resulting in lesions that are difficult for the cells to repair which, in turn, can result in cell death. Other nucleic acid affecting compounds include anthracycline molecules such as doxorubicin, which intercalates between the nucleic acid base pairs of DNA polymers, bleomycin which causes nucleic acid strand breaks, and fraudulent nucleosides. Fradulent nucleosides include pyrimidine and purine nucleoside analogs which are inappropriately incorporated into nucleic polymer structures and ultimately cause premature DNA chain termination. Certain enzymes that affect the integrity and functionality of the genome can also be inhibited in cancer cells by specific chemical agents and result in cancer cell death. These include enzymes that affect ribonucleotide reductase (e.g. hydroxyurea, gemcitabine), topoisomerase I (e.g. camptothecin) and topoisomerase II (e.g., etoposide).

One of the most broadly used of these DNA targeted anticancer drugs is cisplatin (cis-diamminedichloroplatinum II, CDDP). This compound is active against several human cancers including testicular, small-cell lung, bladder, cervical and head and neck cancer.

Although the clinical activity of currently approved antiproliferative agents against many forms of cancers can be shown, improvements in tumor response rates, duration of response and ultimately patient survival are still sought. The invention described herein demonstrates the novel use of the cephalotaxine alkaloids and analogs thereof, including homoharringtonine (HHT) which can potentiate the antitumor effects of chemotherapeutic drugs, in particular, agents affecting the integrity of nucleic polymers such as DNA.

SUMMARY OF THE INVENTION

Methods and compositions are provided for the treatment of a host with a cellular proliferative disease, particularly a neoplasia. In the subject methods, pharmaceutically acceptable cephalotaxine and an antiproliferative agent are administered in an amount sufficient to modulate the cellular proliferative disease.

DETAILED DESCRIPTION OF THE FIGURES

FIG. 1 depicts the general structure of a cephalotaxine analog. R1 and R2 represent substitution groups. Structures for R1 and R2 are shown for the cephalotaxine analog, Homoharringtonine.

DETAILED DESCRIPTION OF THE INVENTION

Methods and compositions are provided for the treatment of a host with a cellular proliferative disease, particularly a neoplasia. In the subject methods, a pharmaceutically acceptable cephalotaxine is administered, preferably systemically, in conjunction with an antiproliferative agent to improve the anticancer effects. In a preferred embodiment, the cephalotaxine provides a chemopotentiator effect.

The agents are provided in amounts sufficient to modulate a cellular proliferative disease. In one embodiment, modulation of a cellular proliferative disease comprises a reduction in tumor growth. In another embodiment, modulation of a disease comprises inhibition of tumor growth. In another embodiment, modulation of a cellular proliferative disease comprises an increase in tumor volume quadrupling time (described below). In another embodiment, modulation of a cellular proliferative disease comprises a chemopotentiator effect. In another embodiment, modulation of a disease comprises a chemosensitizing effect. In other embodiments, modulation of a disease comprises cytostasis. In still other embodiments, modulation of a disease comprises a cytotoxic effect.

A chemical agent is a "chemopotentiator" when it enhances the effect of a known antiproliferative drug in a more than additive fashion relative to the activity of the chemopotentiator or antiproliferative agent used alone. In some cases, a chemosensitizing effect may be observed. This is defined as the effect of use of an agent that if used alone would not demonstrate significant antitumor effects but would improve the antitumor effects of an antiproliferative agent as compared to use of the antiproliferative agent by itself.

As used herein, the term "cephalotaxine" includes all members of that chemical family including alkaloid derivatives of the Chinese evergreen, *Cephalotaxus fortueni* and analogs thereof. The cephalotaxine family is defined by chemical structure as the ring structures in FIG. 1.

Figure 1:
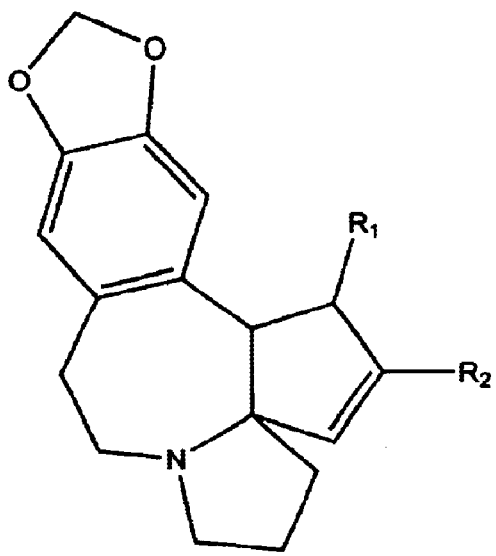
Figure 1:
Figure 1:
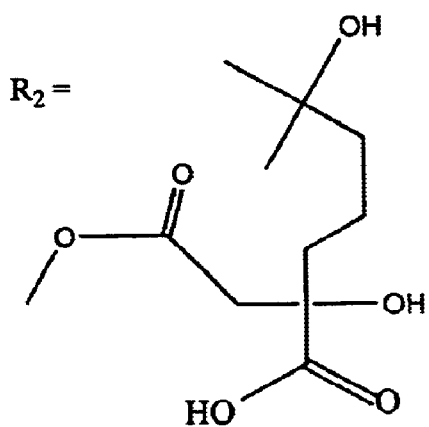

A cephalotaxine analog is further defined but not limited to the structure depicted in FIG. 1, having substituent or substitute groups at R1 and R2. Examples of R1 and/or R2 include esters, including herringtonine, isoharringtonine, homoharringtonine, deoxyharringtonine, acetylcephalotaxine and the like. Table 1 lists structures of R1 and R2 for some of these analogs. R1 and R2 substitutions are typically employed to improve biological activity, pharmaceutical attributes such as bioavailability or stability, or decrease toxicity. In one embodiment, R1 and/or R2 include alkyl substitutions (e.g., methyl, ethyl, propyl etc.). In another embodiment, R1 and/or R2 include esters (e.g., methoxy, ethoxy, butoxy, etc.). R1 and R2 are not limited to the above examples, however, in the scope of this invention.

TABLE 1

| | R1 | R2 |
|---|---|---|
| isoharringtonine | —OCH$_3$ | OH OH<br>\| \|<br>CH$_3$CH(CH$_2$)$_2$C——CHCO$_2$CH$_3$<br>\|<br>CO$_2^-$ |
| harringtonine | —OCH$_3$ | OH OH<br>\| \|<br>CH$_3$C(CH$_2$)$_2$C——CH$_2$CO$_2$CH$_3$<br>\| \|<br>CH$_3$ CO$_2^-$ |
| acetylcephalotaxine | —OCH$_3$ | CH$_3$CO$_2^-$ |
| homoharringtonine | —OCH$_3$ | OH OH<br>\| \|<br>CH$_3$C(CH$_2$)$_3$C——CH$_2$CO$_2$CH$_3$<br>\| \|<br>CH$_3$ CO$_2^-$ |

Figure 2:
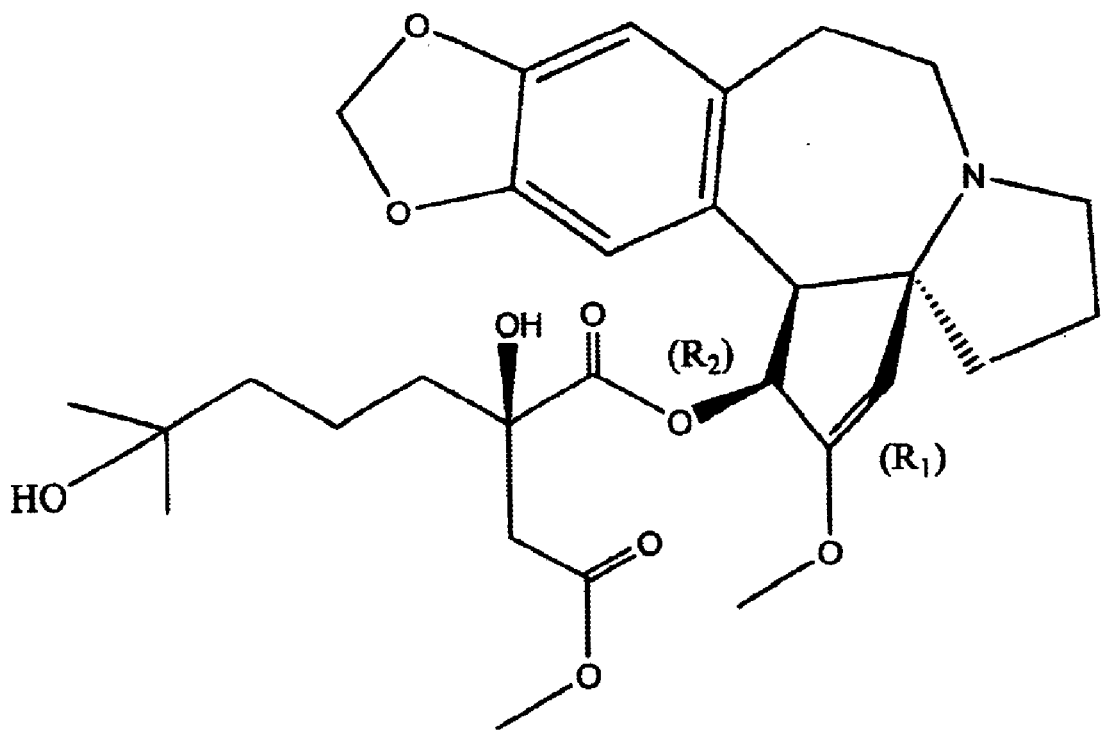
FIG. 2 depicts the structure of the cephalotaxine analog, Homoharringtonine.

A cephalotaxine analog is a further chemical refinement. A specific example of a cephalotaxine analog is homoharringtonine which is the butanediocate ester of cephalotaxine, 4-methyl-2-hydroxy-2-(4-hydroxy-4-methyl pentyl) (FIG. 2).

As used herein, antiproliferative agents are compounds which induce cytostasis or cytotoxicity. "Cytostasis" is the inhibition of cells from growing while "cytotoxicity" is defined as the killing of cells. Specific examples of antiproliferative agents include: antimetabolites, such as methotrexate, 5-fluorouracil, gemcitabine, cytarabine, pentostatin, 6-mercaptopurine, 6-thioguanine, L-asparaginase, hydroxyurea, N-phosphonoacetyl-L-aspartate (PALA), fludarabine, 2-chlorodeoxyadenosine, and floxuridine; structural protein agents, such as the vinca alkaloids, including vinblastine, vincristine, vindesine, vinorelbine paclitaxel, and colchicine; antibiotics, such as dactinomycin, daunorubicin, doxorubicin, idarubicin, bleomycins, plicamycin, and mitomycin; hormone antagonists, such as tamoxifen and luteinizing hormone releasing hormone (LHRH) analogs; nucleic acid damaging agents such as the alkylating agents mechlorethamine, cyclophosphamide, ifosfamide, chlorambucil, dacarbazine, methylnitrosourea, semustine (methyl-CCNU), chlorozotocin, busulfan, procarbazine, melphalan, carmustine (BCNU), lomustine (CCNU), and thiotepa, the intercalating agents doxorubicin, dactinomycin, daurorubicin and mitoxantrone, the topoisomerase inhibitors etoposide, camptothecin and teniposide, and the metal coordination complexes cisplatin and carboplatin.

The following examples are offered by way of illustration and not by way of limitation.

EXAMPLES

Example 1
Chemopotentiation of Cisplatin (CDDP) by Homoharringtonine (HHT)

Transplantable experimental murine fibrosarcomas (2×10$^5$ RIF-1 cells) were grown intradermally in the flanks of 3 month old female C3H mice (Charles River, Holister, Calif.). When the tumors reached a volume of approximately 100 mm$^3$, the mice were randomly assigned to each experimental group (4 mice per group).

The experimental compositions were prepared as described in Table 2.

TABLE 2

| Agent | Dose | Solvent | Supplier |
|---|---|---|---|
| Homoharringtonine | 2 mg/kg | DMSO | NCI |
| Cisplatin | 4 mg/kg | Water for injection | David Bull Labs |

The chemopotentiator, homoharringtonine, was obtained from NCI and was made to the appropriate concentration in DMSO. Cisplatin (David Bull Laboratories-Mulgrave, Australia, lot. 5201844x) was made to the appropriate concentration in water for injection. The compositions were injected systemically (i.e., intraperitoneally, i.p.), in a volume of 100 microliters. For the treatment of group 3, the chemopotentiator, homoharringtonine, was injected 30 minutes prior to the injection of cisplatin. After treatment, the growth of the tumors was monitored three times per week by caliper measurements of three perpendicular diameters of the tumor and calculation of tumor volume from the formula:

$$V = \pi/6 \times D_1 \times D_2 \times D_3,$$

where $D_{1-3}$ is in mm

The tumors were followed until they reached a size of four times their day zero treatment volume (TVQT), or up to 30 days after treatment, whichever came first. The data is expressed as the "tumor volume quadrupling time" (TVQT) mean and as the "delay." Mean TVQT is the mean days required for individual tumors to grow to four times the tumor volume at the initial treatment day. The "delay" is the median of days required for a tumor to grow to four times the mean size of the treated group, minus the median of days required to grow to four times the mean size of the control group. The data is also expressed as the ratio of the tumor volume quadrupling time of the treated tumor over the untreated control group (TVQT/CTVQT). Increasing values of this ratio indicate increased antitumor response.

Figure 3:
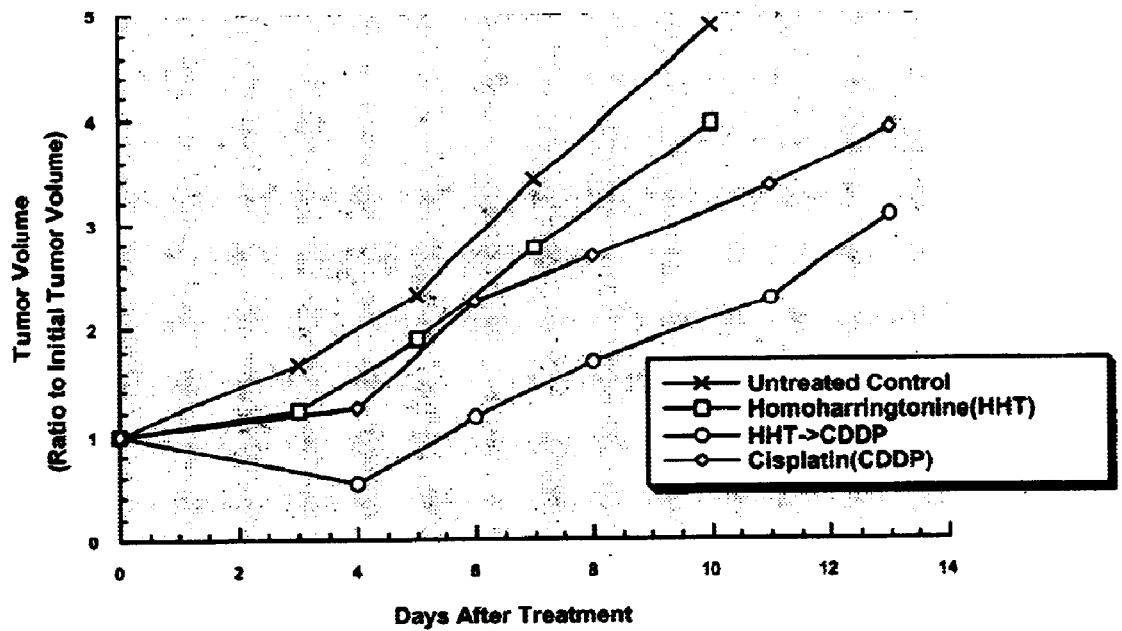
FIG. 3 shows tumor growth delay, as tumor volume on days after treatment with HHT, HHT followed by CDDP, or CDDP alone.

The data is presented in Table 3 below and in FIG. 3.

TABLE 3

| Group | Treatment | Dose (mg/kg) | Mean TVQT ± S.E. | TVQT/CTVQT | Median (TVQT) | Delay (Days) |
|---|---|---|---|---|---|---|
| 1 | Untreated Control | — | 8.3 ± 0.4 | 1.0 | 8.6 | 0.00 |
| 2 | Homo-harringtonine | 2 | 10.1 ± 0.4 | 1.2 | 9.8 | 1.20 |
| 3 | Homo-harringtonine → Cisplatin | 2 → 4 | 14.9 ± 0.8 | 1.8 | 14.8 | 6.17 |
| 4 | Cisplatin | 4 | 12.9 ± 1.1 | 1.5 | 12.5 | 3.83 |

The arrow (→) in Group 3 indicates administration 30 minutes following administration of homoharringtonine.

The results of Table 3 indicate that the antiproliferative activity of cisplatin is enhanced by the use of the chemopotentiator, homoharringtonine in that a more than additive effect was observed when both compounds were used to treat the tumor bearing mice (group 3) in comparison to the use of cisplatin alone (group 4) or homoharringtonine alone (group 2).

Example 2
Effect of Homoharringtonine, Alone and in Combination with Other Chemotherapeutics on RIF-1 Tumor Growth in C3H Mice The RIF-1 murine fibrosarcoma tumor model was used to evaluate the antitumor activity of homoharringtonine, alone and in combination with various antiproliferative agents. The antiproliferative agents used include those that affect nucleic acid (e.g., DNA) integrity (e.g., cisplatin, cytarabine, camptothecin, etoposide, 5-fluorouracil, or amonafide), agents that affect structural proteins (e.g., paclitaxel, vinblastine, or colchicine) or cytoplasmic enzymes (e.g., genistein).

Homoharringtonine (HHT-NCI) was obtained from NCI as a powder. Homoharringtonine (HHT-Clin) was obtained from Hangzhou Minsheng Pharmaceutical Group (Hangzhou, China), in 1 mL vials, prediluted with water to 1 mg/mL. Cisplatin for Injection, USP, was obtained from David Bull Labs (Mulgrave, Australia), Lot No. 5201844x, as a lypholized powder. Paclitaxel was obtained from Bristol Myers Squibb Co. (Princeton, N.J.), Lot No. 9J16241, exp. September 2001, prediluted to 6 mg/mL in Cremaphor/EL. Cytarabine was obtained from Bedford Labs (Bedford, Ohio), Lot No. 86968A, exp. June 2002, as a lypholized powder. Camptothecin was obtained from Boehringer-Ingelheim, Lot No. 142088, as a powder. Vinblastine was obtained from Bedford Labs (Bedford, Ohio), Lot No. 112647, as a lypholized powder. Etoposide was obtained from Pharmacia (Kalamazoo, Mich.), Lot No. ETA013, exp. May 1999, as a liquid prediluted to 20 mg/mL. 5-Fluorouracil was obtained from Pharmacia (Kalamazoo, Mich.), Lot No. FFA191, exp. July 2000, as a liquid prediluted to 50 mg/mL. Amonafide was obtained from Penta Biotech (Union City, Calif.), Lot No. 039-01, as a powder. Colchicine was obtained from Sigma (St. Louis, Mo.), Lot No. 55H0685, as a powder. Genistein was obtained from ChemCon GmbH (Freburg i. Br.), Lot No. CC-6700-26, as a powder. DMSO was obtained from Sigma (St. Louis, Mo.), Lot No. 80K3695 0.9% Sodium Chloride for Injection, USP (saline) was manufactured by Abbott Laboratories (Lot No. 55-199-DK). Sterile Water for Injection, USP (WFI) was manufactured by Lyphomed, Inc. (Lot No. 390849).

Formulations

Test preparations (treatment groups) are summarized in Table 4.

For preparation of formulations 1–4, HHT-NCI was weighed into vials and dissolved in DMSO at the stated concentrations.

For formulation 5, the contents of a 10-mg vial of lyophilized CDDP (Cisplatin for Injection) was resuspended with 10 mL WFI to produce a 1 mg/mL CDDP suspension.

For formulation 6, paclitaxel, prediluted in Cremaphor/EL and dehydrated alcohol to 6 mg/mL was further diluted to 3.3 mg/mL with WFI.

Formulations 7 and 8 were prepared by further diluting HHT-Clin to the stated concentrations with WFI. Formulation 9 was undiluted HHT-Clin, used as received.

Formulation 10 was prepared by adding 1 mL of WFI to 100 mg of cytarabine as a lypholized powder.

Formulation 11 was prepared by adding DMSO to camptothecin at a concentration of 1 mg/mL.

Formulation 12 was made by adding 0.9% Sodium Chloride for Injection to a vial of 10 mg of vinblastine lypholized powder.

Formulations 13–17 were prepared by diluting the appropriate amount of each test agent into saline (13–2.5 mg/mL etoposide, 14–7.5 mg/mL 5-fluorouracil, 15–7.5 mg/mL amonafide, 16–2.5 mg/mL colchicine, 17–3.75 mg/mL 5-fluorouracil).

Formulation 18 was prepared by diluting 15 mg of genistein in 1 mL of DMSO.

Animals

Female C3H mice (Charles River Laboratories, Holister, Calif.), approximately 3 months old, were used for the study. The average body weight was approximately 25 g. Animals were maintained in isolator cages on a 12-hour light-and-dark cycle. Food and water were available ad libitum.

Tumors

The RIF-1 murine fibrosarcoma cell line was maintained in in vitro culture (Waymouth medium supplemented with 20% fetal bovine serum) at 37° C. in a humidified 5% $CO_2$ incubator. Log-phase RIF-1 cells were trypsinized and harvested from cell culture flasks to yield a concentration of $4 \times 10^6$ cells/mL, then injected intradermally in a volume of 50 μL (equivalent to $2 \times 10^5$ cells per injection) into both flanks of each mouse. Nine days later, when tumors reached approximately 100 $mm^3$ in size, the animals were randomized to different treatment groups.

Treatment Groups

Treatment groups are summarized in Table 4. Four to five animals were assigned to each treatment group. The intraperitoneal injection volume was 100 μL. Intratumoral injections (50 μL) were made into one of the two tumors on each animal with the contralateral tumor serving as an untreated control. The oral administration volume was 100 μL. Combination treatments using two test agents were administered as two separate injections, with the second one following the first either immediately or after 30 minutes.

Evaluation of Tumor Volume Quadrupling Time

Tumors were measured three times weekly for up to 22 days with Vernier calipers. Tumor volume (cubic millimeters, $mm^3$) was calculated according to the formula:

$$V = \pi/6 \times D_1 \times D_2 \times D_3$$

in which $D_{1-3}$ are perpendicular diameters measured in millimeters (mm) Tumor volume quadrupling time (TVQT), defined as the time required for a tumor to grow to four times its initial volume (at the time of treatment), was used as a study endpoint. The TVQT was determined for each treatment group and expressed in days as the mean±standard error (SE).

Antitumor activity or modulation of tumor growth (as measured by delayed tumor growth, i.e. increases in TVQT values) by homoharringtonine administered as a single agent or in combination with other chemotherapeutics is presented in Table 5.

Results from eight separate experiments are included in this study. In experiment E010, tumors in untreated control animals quadrupled in size in an average of 7.2 days. Intraperitoneal administration of homoharringtonine from NCI at 5 mg/Kg had a TVQT of 14.5 days and intratumoral administration of homoharringtonine at that dose resulted in a TVQT of 15.6 days.

In experiment E011, untreated control animals quadrupled in size an average of 8.3 days while intraperitoneal administration of homoharringtonine from NCI at 2 mg/Kg extended the mean TVQT to 10.1 days, and the additional intraperitoneal administration of CDDP further extended the mean TVQT to 14.9 days. While paclitaxel (10 mg/Kg), alone, demonstrated a TVQT of 8.8 days, the addition of homoharringtonine (2 mg/kg) did not change the TVQT, making paclitaxel the only agent with combinatorial activity less than that of homoharringtonine, alone.

Homoharringtonine from Hangzhou Minsheng Pharmaceutical Group (Hangzhou, China), formulated in sterile water at either 2 mg/Kg or 4 mg/Kg was used for the remainder of the combination studies.

At 2 mg/Kg, homoharringtonine had an average TVQT of 10.4 days in E026 while the untreated controls quadrupled in 7.4 days. Combination administration of cisplatin (4 mg/Kg) with homoharringtonine (2 mg/Kg) yielded a TVQT of 11.1 days, which was greater than homoharringtonine (TVQT=10.4 days) or cisplatin (TVQT=9.4 days), alone.

In experiment E030, where untreated controls quadrupled in 6.7 days, homoharringtonine treatment (2 mg/Kg) yielded a TVQT of 7.9 days and camptothecin or cytarabine gave TVQT's of 9.4 or 7.6 days, respectively. Combination administration of homoharringtonine (2 mg/Kg) with camptothecin (6 mg/Kg) or cytarabine (400 mg/Kg) increased the TVQT's to 10.1 and 8.6 days, resepectively.

In E032, where untreated controls quadrupled in 6.5 days, homoharringtonine at 4 mg/Kg had an average TVQT of 8.5 days. Administration of homoharringtonine (4 mg/Kg) in combination with 5-fluorouracil (30 mg/Kg) resulted in a TVQT of 17.9 days versus 13.6 days for 5-fluorouracil, alone. Combination administration of homoharringtonine (4 mg/Kg) and vinblastine (2 mg/Kg) yielded a TVQT of 10.9 days versus 8.6 days for vinblastine, alone. Combination administration of homoharringtonine (4 mg/Kg) and cisplatin (4 mg/Kg) or amonafide (30 mg/Kg) yielded TVQT's of 10.4 and 10.2 days, respectively, versus 9.9 and 7.6 days for those agents, alone. Homoharringtonine in combination with etoposide (10 mg/Kg) gave a TVQT of 8.7 days while etoposide, alone, was 8.5 days.

Orally administered colchicine (10 mg/Kg), in E033, yielded a TVQT of 6.3 days, while untreated contols and homoharringtonine (4 mg/Kg) gave TVQT's of 7.8 and 8.3 days. Homoharringtonine in combination with colchicine at these doses increased the TVQT to 9.4 days.

In E036, genistein (60 mg/Kg) in combination with homoharringtonine (4 mg/Kg) had a TVQT of 9.2 days, which was greater than that of genistein, alone (7.1 days).

There were animal deaths in some groups that were recorded as follows. Three of four mice died after treatment of homoharringtonine obtained from NCI and formulated in DMSO at 1.25 mg/mL. Two of five mice died after receiving this formulation intratumorally. Four of four mice died after treatment of this same homoharringtonine formulated to 2.5 mg/mL in DMSO. The combination of homoharringtonine (0.5 mg/mL) in DMSO with paclitaxel (2.5 mg/mL) was lethal to two of four mice, and the combination of homoharringtonine (0.5 mg/mL) in DMSO with cisplatin (1 mg/mL) was lethal to one of four mice. The combination of homoharringtonine (1 mg/mL) in vinblastine (0.5 mg/mL) was lethal to one of four mice given that treatment, and the combination of homoharringtonine (1 mg/mL) and genistein (15 mg/mL) was lethal to two of five mice.

In summary, intraperitoneal administration of homoharringtonine had antitumor activity, i.e. modulated tumor growth, in the RIF-1 murine fibrosarcoma tumor model. Intraperitoneal administration of homoharringtonine in combination with cisplatin, cytarabine, camptothecin, vinblastine, etoposide, 5-fluorouracil, amonafide, colchicine and genistein had antitumor activity levels greater than homoharringtonine alone, or the individual test agents. The best combinatorial activity used 5-fluorouracil, amonafide and vinblastine. Homoharringtonine in combination with paclitaxel had antitumor activity less than homoharringtonine alone. Homoharringtonine obtained from NCI and formulated in DMSO showed some lethal toxicity while homoharringtonine obtained from Hangzhou Minsheng Pharmaceutical Group (Hangzhou, China) and formulated in sterile water for use in humans did not show lethal toxicity at the doses used.

TABLE 4

Summary of Treatment Groups

| Formulation | Treatment | Concentration (mg/mL) | Route of Administration | Injection Volume (μL) |
|---|---|---|---|---|
| 1 | HHT-NCI in DMSO | 1.25 | IP | 100 |
| 2 | HHT-NCI in DMSO | 2.5 | IP | 100 |
| 3 | HHT-NCI in DMSO | 2.5 | IT | 50 |
| 4 | HHT-NCI in DMSO | 0.5 | IP | 100 |
| 5 | CDDP in WFI | 1 | IP | 100 |
| 6 | Paclitaxel in WFI | 2.5 | IP | 100 |
| 7 | HHT-Clin in WFI | 0.5 | IP | 100 |
| 8 | HHT-Clin in WFI | 0.25 | IP | 100 |
| 9 | HHT-Clin in WFI | 1 | IP | 100 |
| 10 | Cytarabine in WFI | 100 | IP | 100 |
| 11 | Camptothecin in DMSO | 2.5 | IP | 100 |
| 12 | Vinblastine in saline | 0.5 | IP | 100 |
| 13 | Etoposide in saline | 2.5 | IP | 100 |
| 14 | 5-Fluorouracil in saline | 7.5 | IP | 100 |
| 15 | Amonafide in saline | 7.5 | IP | 100 |
| 16 | Colchicine in saline | 2.5 | PO | 100 |
| 17 | 5-Fluorouracil in saline | 3.75 | IP | 100 |
| 18 | Genistein in DMSO | 15 | IP | 100 |

TABLE 5

Effect of Homoharringtonine and Homoharringtonine in Combination with Other Chemotherapeutics on RIF-1 Tumor Growth in C3H Mice

| Exp. # | Formulation | Treatment | # of Tumors | TVQT (days) (Mean ± SE) |
|---|---|---|---|---|
| E010 | — | Untreated control | 8 | 7.2 ± 0.1 |
| E010 | 1 | HHT-NCI (5 mg/Kg) | 2* | 14.5 ± 0.9 |
| E010 | 2 | HHT-NCI (10 mg/Kg) | 0* | All Died |
| E010 | 3 | HHT-NCI (5 mg/Kg) | 3* | 15.6 ± 1.8 |
| E011 | — | Untreated control | 8 | 8.3 ± 0.4 |
| E011 | 4 | HHT-NCI (2 mg/Kg) | 8 | 10.1 ± 0.4 |
| E011 | 5 | CDDP (4 mg/Kg) | 8 | 12.9 ± 1.1 |
| E011 | 4, 5 | HHT-NCI-30'-CDDP | 6* | 14.9 ± 0.8 |
| E011 | 6 | Paclitaxel (10 mg/Kg) | 8 | 8.8 ± 0.4 |
| E011 | 4, 6 | HHT-30'-Paclitaxel | 4* | 8.8 ± 0.4 |
| E026 | — | Untreated control | 8 | 7.4 ± 0.3 |
| E026 | 7 | HHT-Clin (2 mg/Kg) | 8 | 10.4 ± 1.0 |
| E026 | 5 | CDDP (4 mg/Kg) | 8 | 9.4 ± 0.5 |
| E026 | 7, 5 | HHT-Clin + CDDP | 8 | 11.1 ± 0.4 |
| E026 | 7, 5 | HHT-Clin-30'-CDDP | 8 | 10.1 ± 0.4 |
| E028 | — | Untreated control | 8 | 8.7 ± 0.5 |
| E028 | 8 | HHT-Clin (1 mg/Kg) | 8 | 9.2 ± 0.7 |
| E028 | 9 | HHT-Clin (4 mg/Kg) | 8 | 10.1 ± 0.4 |
| E030 | — | Untreated control | 8 | 6.7 ± 0.4 |
| E030 | 7 | HHT-Clin (2 mg/Kg) | 8 | 7.9 ± 0.3 |
| E030 | 10 | Cytarabine (400 mg/Kg) | 8 | 7.6 ± 0.2 |
| E030 | 7, 10 | HHT-Clin + Cytarabine | 8 | 8.6 ± 0.4 |
| E030 | 11 | Camptothecin (6 mg/Kg) | 8 | 9.4 ± 0.4 |
| E030 | 7, 11 | HHT-Clin + Camptothecin | 8 | 10.1 ± 0.6 |
| E032 | — | Untreated control | 8 | 6.5 ± 0.6 |
| E032 | 9 | HHT-Clin (4 mg/Kg) | 8 | 8.5 ± 0.5 |
| E032 | 5 | CDDP (4 mg/Kg) | 8 | 9.9 ± 0.6 |
| E032 | 9, 5 | HHT-Clin + CDDP | 8 | 10.4 ± 0.4 |
| E032 | 12 | Vinblastine (2 mg/Kg) | 8 | 8.6 ± 0.4 |
| E032 | 9, 12 | HHT-Clin + Vinblastine | 6* | 10.9 ± 0.4 |
| E032 | 13 | Etoposide (10 mg/Kg) | 8 | 8.5 ± 1.0 |
| E032 | 9, 13 | HHT-Clin + Etoposide | 8 | 8.7 ± 0.5 |
| E032 | 14 | 5-Fluorouracil (30 mg/Kg) | 8 | 13.6 ± 1.9 |
| E032 | 9, 14 | HHT-Clin + 5-Fluorouracil | 8 | 17.9 ± 0.7 |
| E032 | 15 | Amonafide (30 mg/Kg) | 8 | 7.6 ± 0.4 |

TABLE 5-continued

Effect of Homoharringtonine and Homoharringtonine in Combination with Other Chemotherapeutics on RIF-1 Tumor Growth in C3H Mice

| Exp. # | Formulation | Treatment | # of Tumors | TVQT (days) (Mean ± SE) |
|---|---|---|---|---|
| E032 | 9, 15 | HHT-Clin + Amonafide | 8 | 10.2 ± 0.5 |
| E033 | — | Untreated control | 8 | 7.8 ± 0.6 |
| E033 | 9 | HHT-Clin (4 mg/Kg) | 8 | 8.3 ± 0.4 |
| E033 | 16 | Colchicine (10 mg/Kg) | 8 | 6.3 ± 0.3 |
| E033 | 9, 16 | HHT-Clin + Colchicine | 8 | 9.4 ± 0.5 |
| E033 | 17 | 5-Fluorouracil (15 mg/Kg) | 8 | 6.7 ± 0.4 |
| E033 | 9, 17 | HHT-Clin + 5 Fluorouracil | 8 | 8.6 ± 0.3 |
| E036 | — | Untreated control | 8 | 6.8 ± 0.4 |
| E036 | 18 | Genistein (60 mg/Kg) | 8 | 7.1 ± 0.4 |
| E036 | 9, 18 | HHT-Clin + Genistein | 6* | 9.2 ± 0.5 |

*Animal deaths occurred in these groups. See text for details.

I claim:

1. A method of treatment of a host with a cellular proliferative disease, comprising contacting said host with a composition comprising homoharringtonine [cephalotaxine, 4-methyl-2-hydroxy-2-(4-hydroxy-4-methyl pentyl) butanedioate (ester)] and cisplatin, each in an amount sufficient to modulate said cellular proliferative disease, wherein said cellular proliferative disease is a solid tumor.

2. The method according to claim 1, wherein said homoharringtonine is administered before the administration of said cisplatin.

3. The method according to claim 1, wherein said homoharringtonine is administered during the administration of said cisplatin.

4. The method according to claim 1, wherein said homoharringtonine is administered after the administration of said cisplatin.

5. The method of according to claim 1, wherein the modulation of said disease with said composition is greater than that for cisplatin alone.

6. The method according to claim 1, wherein said modulation comprises a reduction in tumor growth.

7. The method according to claim 1, wherein said modulation comprises an inhibition of tumor growth.

8. The method according to claim 1, wherein said modulation comprises an increase in tumor volume quadrupling time.

9. The method according to claim 1, wherein said modulation comprises a chemopotentiator effect.

10. The method according to claim 1, wherein said modulation comprises a chemosensitizing effect.

* * * * *